(12) United States Patent
Meiri

(10) Patent No.: US 7,776,557 B2
(45) Date of Patent: Aug. 17, 2010

(54) METHOD FOR MONITORING TOCOLYTIC TREATMENT

(75) Inventor: Hamutal Meiri, Tel Aviv (IL)

(73) Assignee: Diagnostic Technologies Ltd., Haifa (IL)

( * ) Notice: Subject to any disclaimer, the term of this patent is extended or adjusted under 35 U.S.C. 154(b) by 0 days.

(21) Appl. No.: 12/223,331

(22) PCT Filed: Jan. 28, 2007

(86) PCT No.: PCT/IL2007/000106

§ 371 (c)(1),
(2), (4) Date: Jul. 29, 2008

(87) PCT Pub. No.: WO2007/086067

PCT Pub. Date: Aug. 2, 2007

(65) Prior Publication Data

US 2009/0029397 A1 Jan. 29, 2009

Related U.S. Application Data

(60) Provisional application No. 60/762,863, filed on Jan. 30, 2006.

(51) Int. Cl.
*G01N 33/53* (2006.01)
(52) U.S. Cl. ............... 435/7.1; 435/6; 435/7.2; 435/7.91
(58) Field of Classification Search ............ None
See application file for complete search history.

(56) References Cited

U.S. PATENT DOCUMENTS

| 5,198,366 | A | | 3/1993 | Silberman |
| 5,370,135 | A | | 12/1994 | Dullien |
| 6,458,574 | B1 | * | 10/2002 | Selden et al. .......... 435/208 |
| 6,790,625 | B1 | | 9/2004 | Paltieli et al. |

2003/0092188 A1 5/2003 Admon et al.

FOREIGN PATENT DOCUMENTS

| WO | WO 9603929 | * | 2/1996 |
| WO | WO 2004/021012 A2 | | 3/2004 |

OTHER PUBLICATIONS

Sammar et al. (American J. Obstetrics Gynecology 2005 vol. 193, p. S77, #238.*
Burger, O. et al., "Placental Protein 13 (PP-13): Effects on cultured trophoblasts, and its detection in human body fluids in normal and pathological pregnancies," Placenta, 2004, pp. 608-622, vol. 25, Elsevier Ltd.
Bartz, C. et al., "Tocolytic substances dammage syncytiotrophoblast demonstrated by release of placental protein 13," Hypertension in Pregnancy, 2006, p. 56, vol. 25.
Bartz, C. et al., "Do tocolytic agents damage the placental trophoblast? Measurements of placental protein 13 in maternal blood," Journal of the Society for Gynecologic Investigation, Feb. 2006, p. 220A, vol. 13 (2), Elsevier Science.
Than, N.G. et al., "Functional analyses of placental protein 13/galectin-13," European Journal of Biochemistry 2004, pp. 1065-1078, vol. 271.
Than, N.G. et al., "Isolation and sequence analysis of a cDNA encoding human placental tissue protein 13 (PP13), a new lysophospholipase, homologue of human eosinophil charcot-leyden crystal protein," Placenta, 1999, pp. 703-710, vol. 20, Harcourt Publishers Ltd.

* cited by examiner

*Primary Examiner*—Jacob Cheu
(74) *Attorney, Agent, or Firm*—The Nath Law Group; Susanne M. Hopkins

(57) ABSTRACT

A method of monitoring tocolytic therapy in a pregnant woman. The method comprises determining a first concentration of placental protein 13 (PP13) in a bodily substance of a woman who has not received treatment with a tocolytic agent, determining a second concentration of PP13 in a bodily substance of the pregnant woman after initiation of treatment with a tocolytic agent, and comparing the second concentration with the first concentration. Based on the comparison, it may be determined whether to continue, discontinue, or modify the tocolytic treatment.

13 Claims, 4 Drawing Sheets

METHOD FOR MONITORING TOCOLYTIC TREATMENT

CROSS-REFERENCE

This is a National Phase Application filed under 35 U.S.C. 371 of International Application No. PCT/IL2007/000106, filed on Jan. 28, 2007, claiming the benefit under 35 USC 119(e) of U.S. Provisional Patent Application No. 60/762,863, filed on Jan. 30, 2006, the entire contents each of which are hereby incorporated herein by reference in their entirety.

FIELD OF THE INVENTION

This invention relates to a method for monitoring the efficacy of a tocolytic treatment of a pregnant woman.

BACKGROUND OF THE INVENTION

Premature birth or preterm delivery (PTD) is defined as any delivery occurring before 37 weeks of gestation. PTD is an undesirable complication of pregnancy responsible for a variety of impairments in the newborn baby due to lower birth weight, motor and cognitive disabilities, and, in very severe cases, in-partum or after partum death. In cases of pregnancy complications, maintaining pregnancy for the full term (37-41 weeks) is important for two major reasons. One is to allow the pregnant woman to reach a tertiary level medical center before birth, an issue of great significance in community clinics and rural-based health service settings. The other is to buy time to administer treatments and drugs such as antenatal corticosteroids that facilitate the maturation of fetal organs. There is therefore a need in certain cases to extend pregnancy duration so as to reduce the severity of the consequences of pre-maturity.

Tocolytics are a group of medications clinically utilized to stop contractions, thereby reducing the risk of PTD. Tocolytics delay parturition and thus decrease prenatal mortality and morbidity. Evidence has been reported that tocolytics delay delivery by 1-7 days, thus allowing for a significant time to administer drugs such as antenatal corticosteroids. Tocolytics are routinely administrated when a pregnant woman with gestational age between 20 and 37 weeks (confirmed by dating the gestational age according to the last menstrual period or by ultrasound) has frequent, regular uterine contractions (preferably documented by a tocodynamonmeter) and/or when she shows progressive change in the cervix or a cervical dilation greater than 2 cm and effacement greater than 80%. However, tocolytics may have adverse effects either directly or as a result of inappropriate prolongation of pregnancy in an adverse intrauterine environment, e.g. uterine abruption. The prophylactic use of tocolytic agents can be associated with side effects such as maternal pulmonary edema, especially in women carrying twins, chorioamnionitis, and dehydration. Placenta abruption and intrauterine growth restriction are among the contra-indications for the use of tocolytic agents.

In all cases of patients at gestation week 34-37, any of the above symptoms will indicate initiation of treatment, adjusted individually to each patient. For patients of less than 34 weeks, where a risk for preterm labor is identified early, tocolytic agents are often given 2-4 times prophylactically from 32-34 weeks of gestation, subject to laboratory testing indicating it is allowed. During tocolytic agent administration it is necessary to continuously monitor fetal heart rate and uterine activity, pulmonary status, cardiovascular status, glucose level and clotting factors; Ultrasound is required to confirm date and rule out anomalies, pelvic exam is made to confirm cervical status, and laboratory studies including CBC, urine for culture and sensitivity follow the health status while group B beta hemolytic strep culture or rapid identification test are carried out. In rare cases, amniocentesis is done in febrile patients.

A number of tocolytic agents have been used in the clinic. Initially, the beta agonists (beta mimetic), especially ritodrine and terbutaline, were extensively used, but were found to have adverse maternal side effects.

The calcium channel blockers came next. These included the following:

A. Magnesium Sulfate ($MgSO_4$)—Neonatal neuromuscular blockade and difficult resuscitation may be associated with excessive use of magnesium sulfate. In addition, there are conflicting data as to the neuroprotective effect of magnesium sulfate. Despite the debate of the efficacy of $MgSO_4$ and its side effects, it remains the first-line tocolytic agent in many institutions.

B. Nifedipine is associated with a greater chance of delivery delay, less maternal side effects and less neonatal respiratory distress syndrome than the beta agonists. There is a theoretical risk to the fetus, based on animal studies, although human clinical studies have so far failed to show a similar result.

Another group of tocolytics are non-steroidal anti-inflammatory drugs (NSAID) such as indomethacin and glyceryl-tri-nitrite which have fewer side effects and better efficacy as measured by lowering the occurrence of low birth weight and prolonging pregnancy. Due to the slow effect of indomethacin, it is often given together with a tocolytic of one of the other groups. The oxytocin antagonist, atosiban, has a comparable effect on delivery delay to the beta agonists but with fewer maternal side effects. Its relatively higher price limits its wide use clinically.

Many of the side effects related to the administration of tocolytics, either given i.v, or per-os, are related to the damage they cause to the placenta, such as facilitated apoptosis, damage to maternal artery blood flow and the level of placental tissue oxidation and nutrition. In some cases, the damage to the placenta can lead to several complications and exacerbate conditions such as intrauterine growth restriction (IUGR). There is no method currently available to detect the impact of tocolytic agents on the placenta, and thereby on the fetus and the mother.

Thus, a balance must be struck between administrating a too high dose of tocolytics, which can damage the placenta, fetus and/or mother, and a too low dose which will not be effective in preventing PTD. It is therefore desirable to have a means for monitoring the effect of a specific type and dose of tocolytics on the pregnant woman.

U.S. Pat. No. 5,370,135 discloses a method for monitoring the efficacy of tocolytic treatments by monitoring estriol concentrations in a body fluid before or during treatment with a tocolytic agent. A first concentration of estriol is measured in a body fluid of a pregnant patient undergoing or diagnosed as a candidate for undergoing treatment with a tocolytic agent, and is correlated with a predetermined standard estriol value. Analysis of the correlation allows a physician to reach better decisions on whether to begin or continue the tocolytic treatment or whether the treatment should be discontinued or modified.

Placental Protein 13 (PP13) is a protein of 15-16,000 MW which may be purified from human placental tissue or prepared by recombinant technology as described in U.S. Pat. No. 6,548,306 (Admon, et al), the contents of which are incorporated herein by reference. Purified PP13 was used to develop an assay for the detection of some pregnancy-related disorders such as intrauterine growth restriction (IUGR), preeclampsia and preterm delivery as described in U.S. Pat. No. 5,198,366 (Silberman), the contents of which are incorporated herein by reference. Both a radioimmunoassay (RIA) and an enzyme-linked immunosorbent assay (ELISA) were developed using labeled PP13 and anti PP13 polyclonal antiserum.

Amino acid composition and sequence analysis of PP13 revealed highest homology to the galectin family—a group of proteins with high affinity to sugar residues which is particularly important in bridging cells to the extracellular matrix (and in differentiation) (Than, N. G., et al (1999) Placenta 20:703-710; Than, et al., (2004) Eur. J Biochem. 271(6): 1065-1078). Indeed PP13 was found by immunohistochemistry to be important in placentation.

U.S. Pat. No. 6,790,625 discloses monoclonal antibodies to PP13 and a solid-phase immunoassay capable of measuring maternal serum PP13 during the early stages of pregnancy.

WO 04/021012 discloses a diagnostic method for pregnancy complications based on a number of factors, including PP13 level.

SUMMARY OF THE INVENTION

It is an object of the present invention to provide a simple in-vitro assay that will allow an attending physician to monitor the efficacy of tocolytic treatment so that continued tocolytic treatment can be adjusted to the minimum effective pharmacological level without damaging the woman or her fetus.

The present invention thus provides a method of monitoring tocolytic therapy in a pregnant woman, comprising:
(a) determining a first concentration of placental protein 13 (PP13) in a bodily substance of a woman who has not received treatment with a tocolytic agent;
(b) determining a second concentration of PP13 in a bodily substance of the pregnant woman after initiation of treatment with a tocolytic agent; and
(c) comparing the second concentration with the first concentration, and, based on the comparison, determining whether to continue, discontinue, or modify the tocolytic treatment.

It has been found that women, exposed to tocolytics during pregnancy, show a transient increase of PP13 release to the maternal blood within the first 24-48 hours after administration. With multiple administrations of tocolytic agents—the level of tocolytic agent-associated release of PP13 increases. Since in pregnancy complications where damage has occurred to the placenta, such as in preeclampsia, the level of PP13 released from the placenta into the maternal blood is higher than normal, the increased release of PP13 subsequent to tocolytic administration reflects the occurrence of damage to the placenta caused by the tocolytic agent.

In the present specification, the term first concentration relates to the level of PP13 in a body fluid of a woman who has not undergone tocolytic treatment. This may be a measured value from the pregnant woman before undergoing tocolytic treatment, or may be based on the standard median values as obtained by statistical methods from the woman undergoing tocolytic treatment or from a statistically significant plurality of pregnant women at the respective gestational week. In the later case, if the woman is known to be in a specific risk group (such as PE, CI or PTD), the median is based on respective PP13 values of a plurality of women from that specific group. If, on the other hand, it is unknown whether the woman belongs to a specific risk group, the median is based on respective PP13 values of a plurality of unaffected (normal) pregnant women. This term may also relate to a plurality of time points during pregnancy which correspond to the period during which the woman is undergoing tocolytic treatment, such as a "virtual baseline", as defined below.

In the present specification, an "untreated" woman is a woman, and in particular a pregnant woman, who has not received treatment with a tocolytic agent, unless otherwise indicated.

The term second concentration refers to the level of PP13 in a body fluid of a pregnant woman undergoing tocolytic treatment. This will always be a measured value taken at various time points during and after the tocolytic treatment, preferably within the first 1 to 4 days after treatment onset, more preferably within the first 24 hours after beginning the administration of the treatment, and thereafter for several days and up to 14-21 days from treatment onset. Samples of the bodily substance are taken preferably every other day, more preferably every day, most preferably twice a day. The term may relate to the highest single measured value, or to a series of values measured at successive time points during and after the treatment.

The term plotted on a graph includes both manually plotting as well as plotting by mathematical calculations, such as is carried out by a computer.

As stated above, the first and second concentrations of PP13 may be either a single measurement or a series of measurements of PP13 concentration. This leads to two possible ways of comparing the concentrations:

(a) the comparison is made between single measurements of the first concentration and the second concentration. A comparison is made between a single measurement taken before and after tocolytic treatment, the later measurement being the highest value of all measurements taken within the first two weeks after initiation of the treatment. Such a comparison will be referred to at times as "the ratio";

(b) the comparison is made between a plurality of the first concentrations and a plurality of the second concentrations determined at corresponding time points of the pregnancy of the woman. The term "corresponding time points" refers to measurements made during the respective gestational week. In one embodiment, a curve may be plotted on a graph based on a series of values measured at successive time points (such as gestational weeks) during and after the tocolytic treatment. The area under the curve (AUC) is calculated, using a "virtual baseline" as the base. Such a comparison will be referred to at times as "the area" or "the AUC".

The virtual baseline may be calculated based either on PP13 values measured for the woman undergoing tocolytic treatment, or on a set of median PP13 values according to the values anticipated if the tocolysis were not administrated. In the first case, a curve is calculated based on measured PP13 values which are unaffected by the tocolytic treatment, i.e. either before treatment or 2 or more weeks after treatment. In the later case, if the woman is known to belong to a specific risk group, the median is taken from that group. If the woman is not known to belong to a specific group, then the median is taken from the unaffected group. The virtual baseline is calculated as follows:

The standard baseline of the PP13 level of an individual patient may be calculated using a standard curve fitting method based on a polynomial of:

$$Y = a_1 X^0 + a_2 X^1 + a_3 X^2 + a_4 X^3 \text{ etc.}$$

where X is gestation week or gestation day $a_1 \ldots$ to $\ldots a_n$ are provided by the curve fitting method The power of X (between 1-5) is selected according to the one that provides the best fit (corresponding to the highest regression coefficient).

An example of a normal polynomial is $Y=465.82-433.22X+245.74\ X^2-64.959\ X^3+8.3323X^4-0.4028X^5$.

An analysis of the ratio or the area will indicate whether the amount of tocolytic agent delivered to the utero-placenta-fetal target exceeds a certain threshold above which the damage caused by the tocolytic treatment is greater than its benefit. This in turn will assist the physician to decide whether to: (a) administer a second dose of the same tocolytic agent; (b) administer a different tocolytic agent; (c) administer a cocktail of tocolytic agents; or (d) discontinue the treatment.

The bodily substance of the woman which is analyzed for PP13 content may be any bodily fluid or tissue which contains measurable amounts of PP13. Examples of bodily substances include maternal blood, saliva, urine, amniotic fluid and umbilical cord blood. Preferably, maternal venal blood or serum is used.

The PP13 protein or its respective RNA/DNA may be measured by any quantitative PP13 assay such as by ELISA, RIA, immunodiagnostic or real time PCR, RT-PCR or siRNA. Typically, the concentration is measured in units of pg/ml.

For the ratio comparison of the second concentration to the first concentration, values of less than 1.4 indicates that the tocolytic treatment should be increased or replaced with a more potent tocolytic drug (the threshold range).

A ratio of the second concentration to the first concentration in the range of 1.4 to 2.9 indicates that the tocolytic treatment should be continued (the effective range).

A ratio of the second concentration to the first concentration above 3 indicates that the tocolytic treatment should be reduced, discontinued or replaced by a less potent drug (the toxic range).

When considering the AUC for the comparison, ratios of less than 4, 4 to 10 and greater than 10 correspond to the threshold, effective and toxic ranges, respectively.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 1A shows a comparison of women who delivered at term a normal baby (normal term), women who had cervix insufficiency (CI) and women who developed preeclampsia around term (PE). FIG. 1B shows a comparison of normal term, CI and women who delivered preterm not due to CI or PE (PTD);

DETAILED DESCRIPTION OF EXEMPLARY EMBODIMENTS

Methods

In all experiments, PP13 was measured (blinded to pregnancy outcome) in maternal venous serum by solid-phase sandwich ELISA assay. PP13 level was calibrated according to standard curves prepared from calibrated standards of recombinant PP13. Concentrations are given in pg PP13/ml serum.

This clinical study was approved by the medical center internal review ethical committee, and all women enrolled in the study provided informed consent to allow the use of a small volume of their blood to determine the level of PP13. Patients were not randomized for any treatment but the decision to treat was based on the standard of medical care in the hospital as best suited to each individual patient.

Example I

Figure 1A:
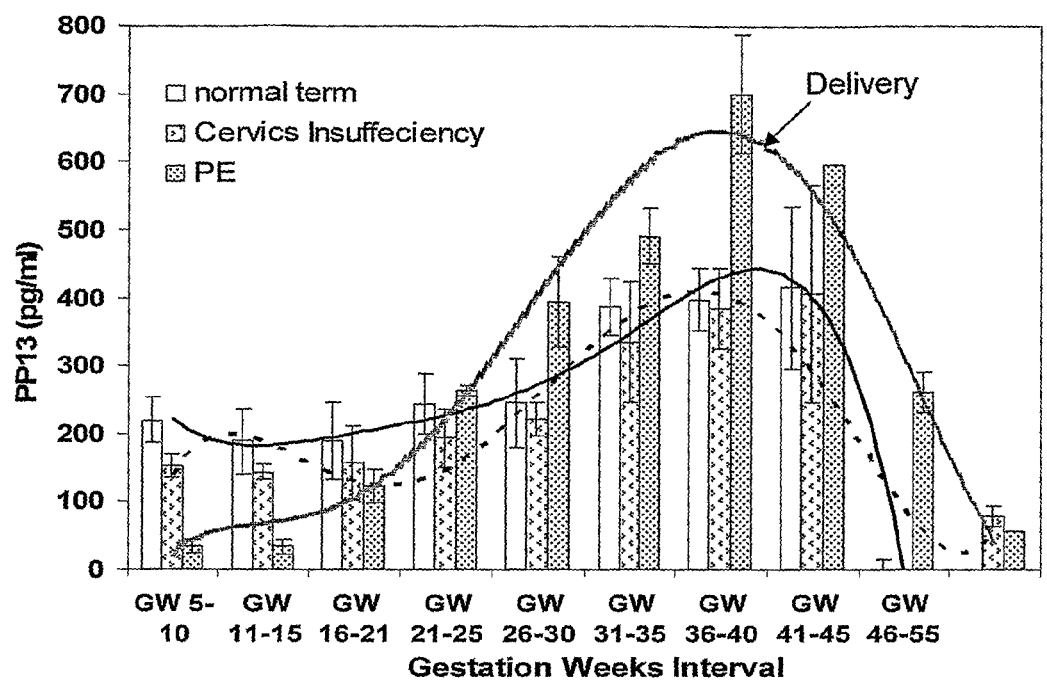
FIGS. 1A & 1B show plots of the change in concentration of PP13 (pg/ml) in blood of women with normal and abnormal pregnancies as measured by testing their blood at 5-week gestation intervals.
Figure 1B:
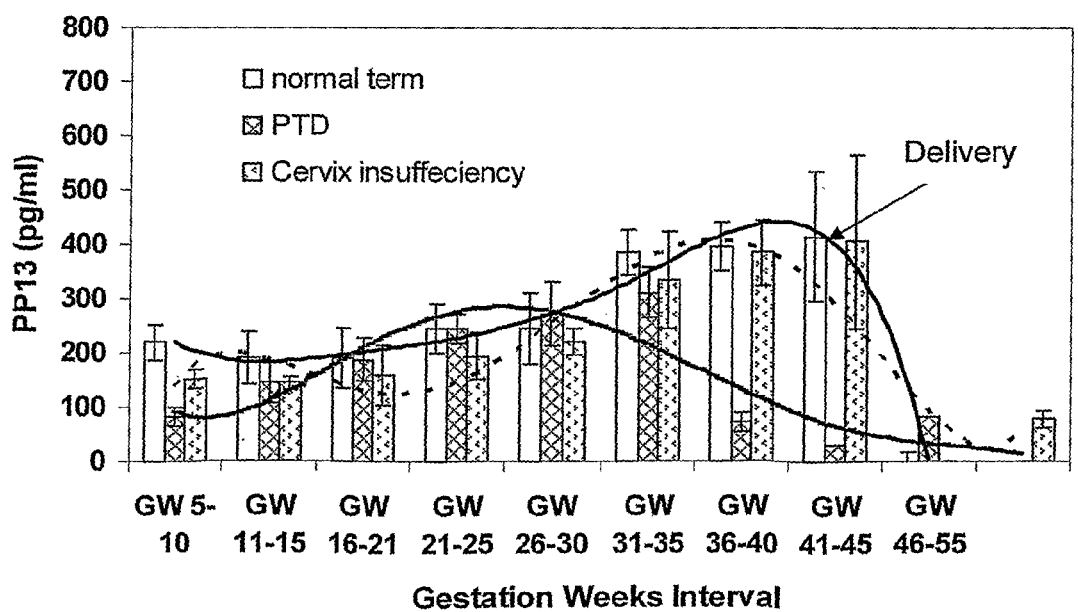

PP13 was monitored continuously in the venous serum of 49 women who delivered at term a normal baby (normal women), 4 who developed preeclampsia around term (PE), 9 who had cervix insufficiency (CI) and delivered at term (6) or preterm (3), and 11 who delivered preterm (PTD) not due to CI or PE. The results are shown in FIGS. 1A and 1B.

It may be seen that in normal women the level of PP13 varies during the course of pregnancy with a gradual increase from the first into the third trimester. In the PE group, the level of PP13 during the third trimester was approximately 50% higher than in the normal group, while the PP13 level in the CI group was very similar to the normal level, which is consistent with CI being a cervical disorder not related to the placenta. In the PTD group, the results show that the PP13 level is lower than normal during the first trimester. During the second trimester the PP13 level reaches the normal level while in the third trimester, the level of PP13 drops below the normal level. After delivery, PP13 disappears from the serum of pregnant women.

These results indicate that beginning from gestational week 16 and on, an increased level of PP13 reflects damage to the placenta, which is the case in PE but not in CI.

Example II

Figure 2A:
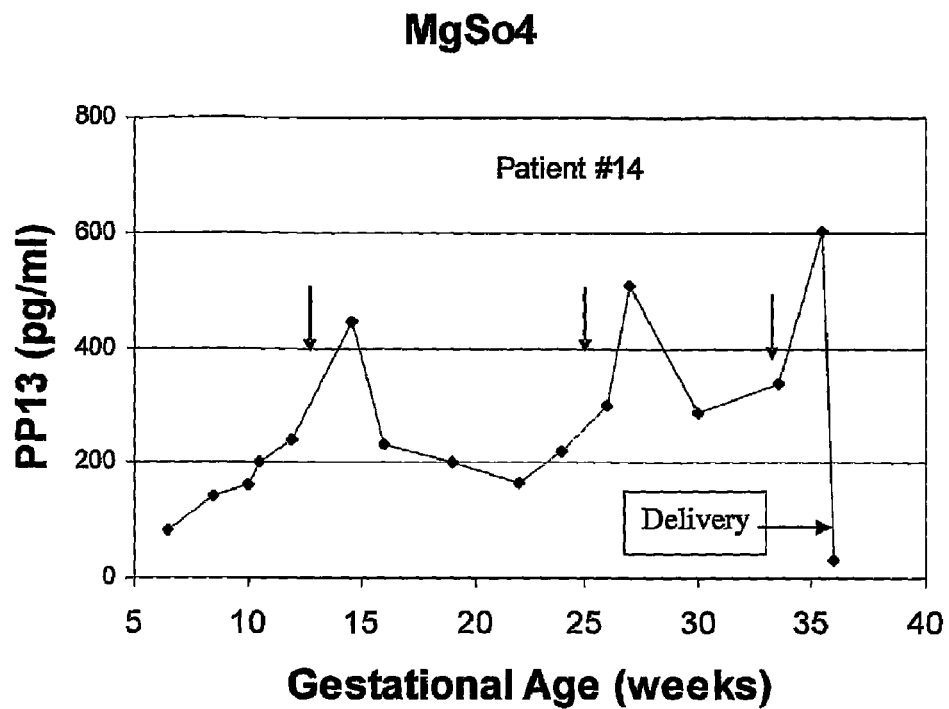
FIGS. 2A & 2B show PP13 levels over time in two patients who received (2A) MgSO$_4$ (downward arrows) or (2B) a combination of MgSO$_4$ (downward arrows) followed by nifedipine (upward arrows). The lower baseline in FIG. 2B indicates the expected level of PP13 if no tocolytic agent had been given (virtual baseline). The time of delivery is indicated.

Two pregnant patients were treated with tocolytic agents to prevent PTD. Both patients delivered preterm. In FIG. 2A, the patient was treated with three doses of 1.4 mM MgSO$_4$ by intravenous administration over a period of 24 hr, while in FIG. 2B, the patient was treated first with several doses of the MgSO$_4$ treatment followed by later repeated administration of nifedipine given orally. The location of the downward arrows indicates the time of administration of MgSO$_4$ while upward arrows represent the time of nifedipine administration.

Figure 2B:
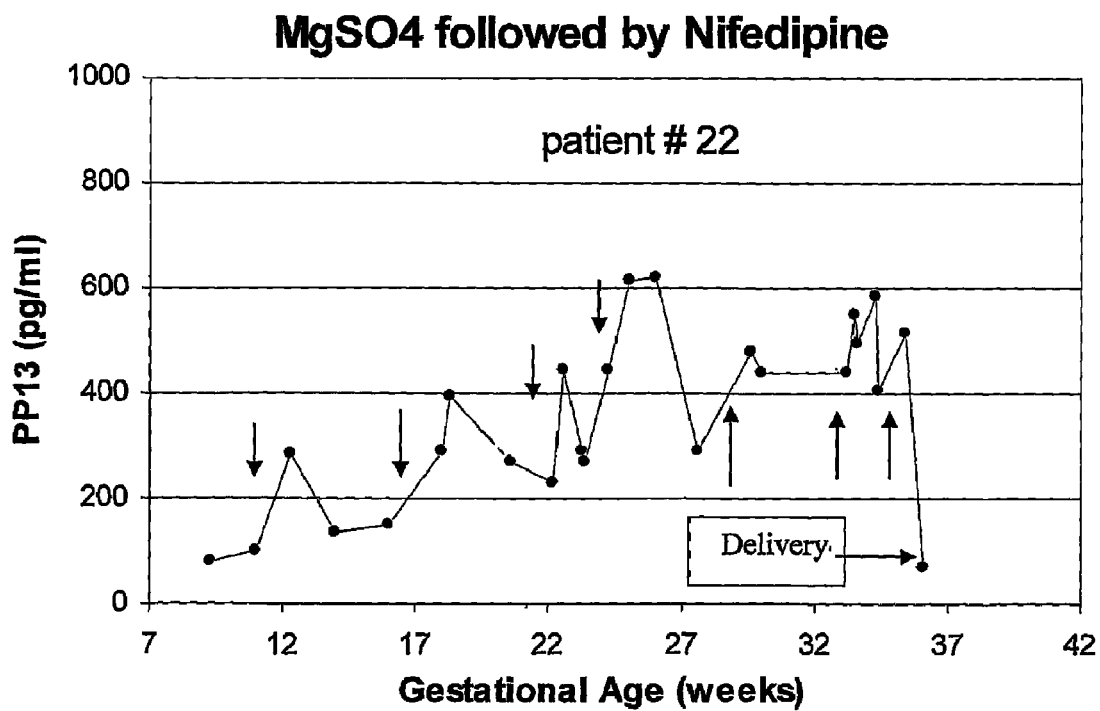

It may be seen from FIGS. 2A and 2B that the administration of a tocolytic agent results in a transient 2-3 fold increase in PP13 levels shortly after the administration. The PP13 level returns to its previous value after several days. This indicates that the tocolytic agent was expected to have the desired effect without causing unacceptable damage to the placenta.

Example III

Figure 3:
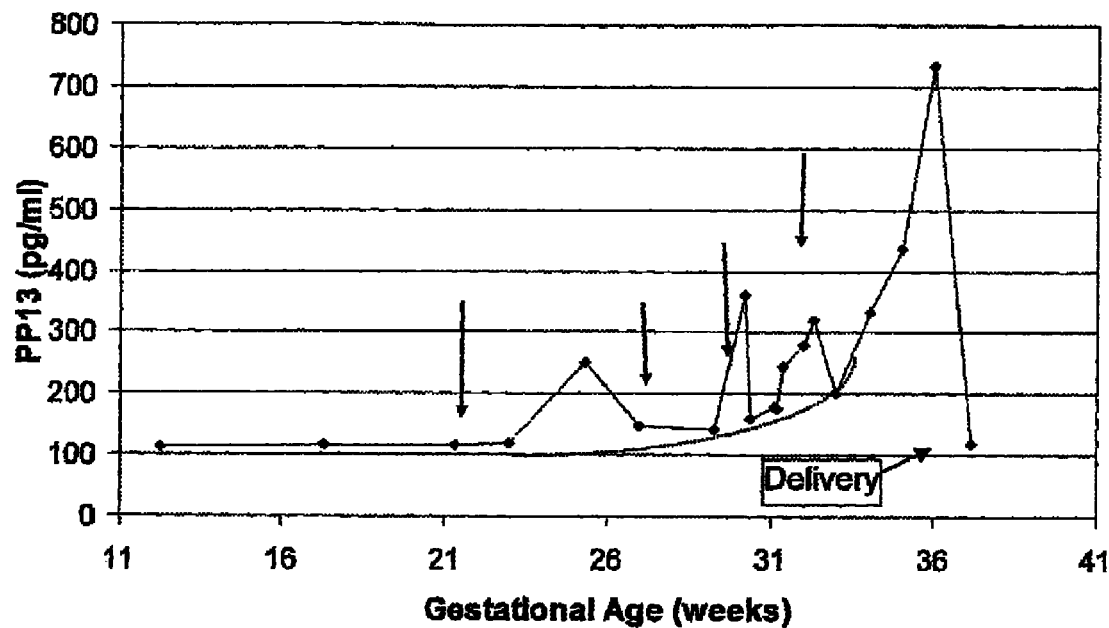
FIG. 3 shows PP13 levels over time in a patient who received atosiban. The meanings of the arrows are as defined in FIG. 2.
Figure 4:
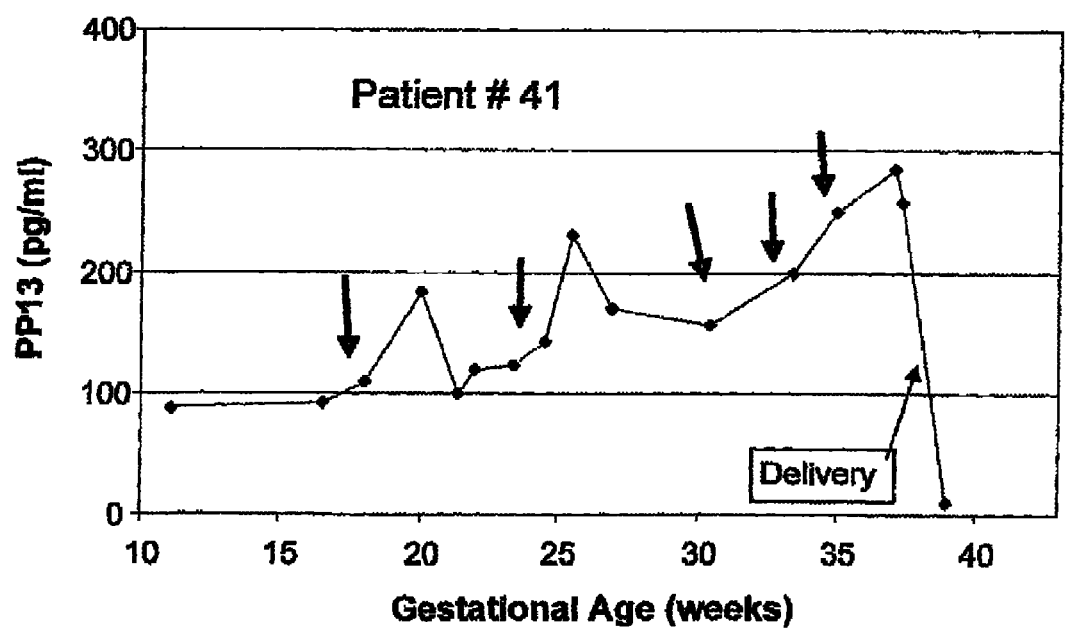
FIG. 4 shows PP13 levels over time in a patient who received nifedipine. The meanings of the arrows are as defined in FIG. 2.

FIGS. 3 and 4 show the PP13 levels in patients who received multiple doses of, respectively, the tocolytic agents atosiban (by IV administration over 24 hours) or nifedipine (orally by tablets). 2-5 fold transient increases are seen after each administration. The baseline gradually increases with each successive administration to a level higher than detected in the blood of pregnant women who go on to deliver either at or pre term. This indicates that the tocolytic treatment began to cause damage to the placenta, as seen with preeclampsia, and the dose should have been somewhat decreased in strength, or the tocolytic agent replaced.

Example IV

Figure 5:
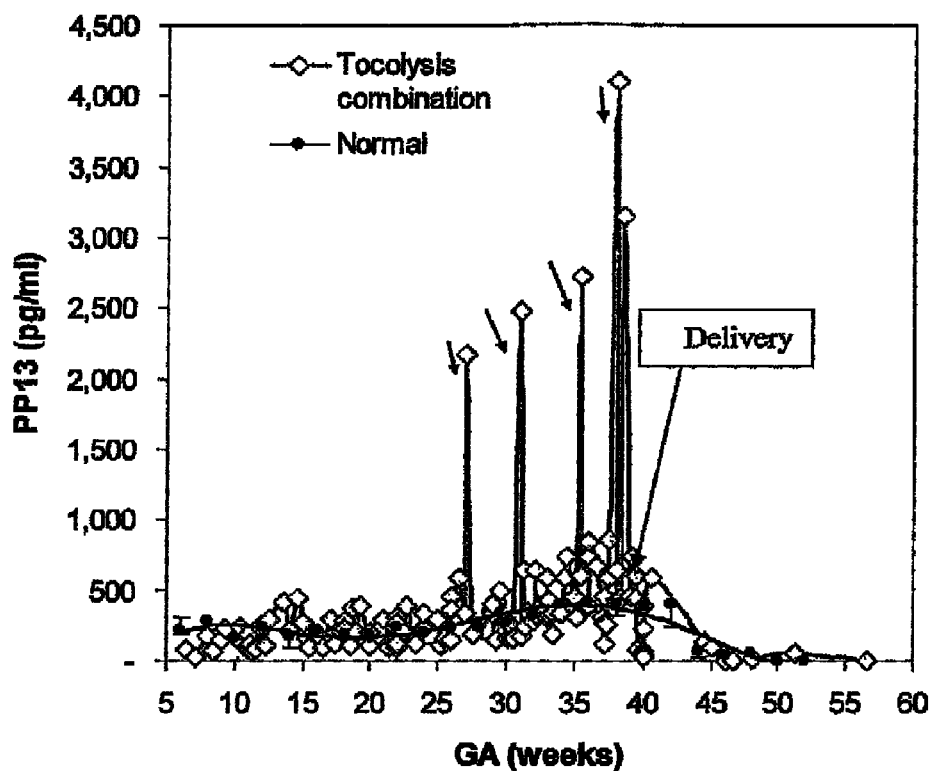
FIG. 5 shows PP13 levels over time (gestation weeks=GA) in a patient who received a simultaneous combination of atosiban and nifedipine. The meanings of the arrows are as defined in FIG. 2.

In this example, the patient received simultaneously a combination of atosiban (by IV administration over 24 hours) and nifedipine (orally by tablets). As can be seen from FIG. 5, this lead to a 10 fold increase in PP13 levels, indicating that either one of the drugs should have been discontinued, the amount of tocolytic agents should have been decreased, the agents replaced by less potent drugs, or the treatment discontinued.

Example V

Figure 6:
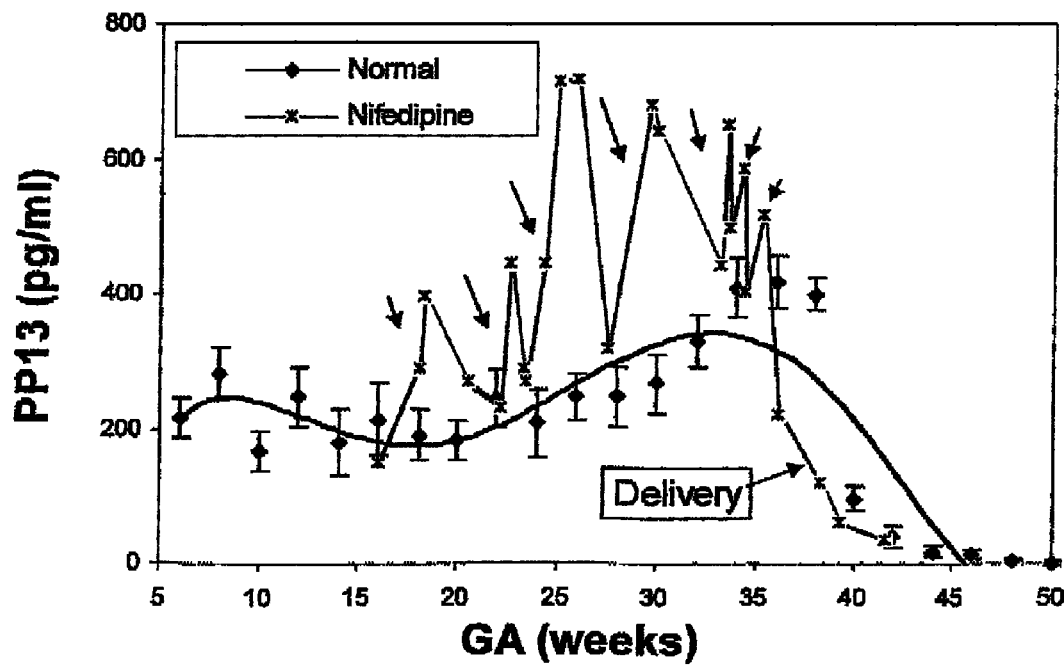
FIG. 6 shows a comparison of PP13 level as a function of time (gestation weeks) in unaffected (normal) women and in a woman treated with the tocolytic agent nifedipine. The meanings of the arrows are as defined in FIG. 2.

A pregnant woman with an increased risk for preterm delivery was treated with nifedipine. FIG. 6 shows the level of PP13 measured by ELISA in the maternal venal blood of the woman. Prior to treatment, at 32 weeks, the value was 200 pg/ml. Within 48 hr after the administration of the tocolytic agent, the level reached 400 pg/ml.

The ratio index is 400/200=2. This indicates that the tocolytic therapy has reached the target to exert its beneficial effect in preventing preterm delivery without endangering the integrity/function of the utero-placenta-fetal system.

However, with repeated administration of the agent the level increased to 720 pg/ml over a baseline of 200 pg/ml yielding a ratio of 3.6. In repeated administrations the level was elevated again to reach a toxic level. These elevated levels are not just higher but continue to be higher for a longer period creating an area of elevated level 5.8 and 4.7 times, respectively, above normal and preterm delivery.

In such a case, if the physician considers that repeating the treatment is required, he may better consider choosing a lower dose and/or changing the tocolytic agent.

The invention claimed is:

1. A method of monitoring tocolytic therapy in a pregnant woman, comprising:
   (a) determining a first concentration of placental protein 13 (PP13) in a bodily substance of a woman who has not received treatment with a tocolytic agent, wherein the bodily substance of the woman is selected from the group consisting of maternal blood, saliva, urine, amniotic fluid, and umbilical cord blood;
   (b) determining a second concentration of PP13 in a bodily substance of the pregnant woman after initiation of treatment with a tocolytic agent, wherein the bodily substance of the woman is selected from the group consisting of maternal blood, saliva, urine, amniotic fluid, and umbilical cord blood; and
   (c) comparing said second concentration with said first concentration, and, based on said comparison, determining whether to continue, discontinue, or modify said tocolytic treatment.

2. The method of claim 1, wherein said untreated first concentration of PP13 is determined from a source selected from the group consisting of:
   (a) a predetermined range of median PP13 concentrations for said bodily substance in a plurality of untreated pregnant women at a similar condition of pregnancy; or
   (b) a previously measured PP13 concentration of the bodily substance of said pregnant woman prior to receiving said tocolytic treatment.

3. The method of claim 1, wherein the comparison is made between single measurements of said first concentration and said second concentration.

4. The method of claim 1, wherein the comparison is made between a plurality of said first concentrations and a plurality of said second concentrations determined at corresponding time points of the pregnancy of the woman.

5. The method of claim 4, wherein the plurality of each of the concentrations is plotted on a graph of concentration vs. time, thereby obtaining a curve, an area under the curve (AUC) is calculated, and the comparison is made between the AUC of said first concentrations and that of said second concentrations.

6. The method of claim 1 wherein the second concentration is measured within 14 days after initiation of the tocolytic treatment.

7. The method of claim 4 wherein the plurality of concentrations is determined over a period of 2-3 weeks after initiation of the tocolytic treatment.

8. The method of claim 1, wherein a ratio between the second concentration to the first concentration of less than 1.4 indicates that the tocolytic treatment should be increased or replaced.

9. The method of claim 1, wherein a ratio between the second concentration to the first concentration in the range of 1.4 to 2.9 indicates that the tocolytic treatment should be continued.

10. The method of claim 1, wherein a ratio between the second concentration to the first concentration above 3 indicates that the tocolytic treatment should be discontinued or replaced.

11. The method of claim 5, wherein a ratio between the AUC of the second concentrations to that of the first concentrations of less than 4 indicates that the tocolytic treatment should be increased or replaced.

12. The method of claim 5, wherein a ratio between the AUC of the second concentrations to that of the first concentrations in the range of 4 to 10 indicates that the tocolytic treatment should be continued.

13. The method of claim 5, wherein a ratio between the AUC of the second concentrations to that of the first concentrations above 10 indicates that the tocolytic treatment should be discontinued or replaced.

* * * * *